United States Patent

Schromm et al.

[11] 3,966,814
[45] June 29, 1976

[54] 1-PHENYL-2-(NAPHTHYLALKYL-AMINO)-ETHANOLS AND SALTS THEREOF

[75] Inventors: Kurt Schromm; Anton Mentrup; Ernst-Otto Renth, all of Ingelheim am Rhein; Werner Traunecker, Munster-Sarmsheim, all of Germany

[73] Assignee: Boehringer Ingelheim GmbH, Ingelheim am Rhein, Germany

[22] Filed: June 27, 1973

[21] Appl. No.: 373,933

Related U.S. Application Data

[63] Continuation of Ser. No. 92,527, Nov. 24, 1970, abandoned.

[30] Foreign Application Priority Data
Dec. 12, 1969 Germany.......................... 1962497

[52] U.S. Cl.......................... 260/570.6; 260/254; 260/348 R; 260/456 R; 260/456 P; 260/471 A; 260/488 R; 260/490; 260/501.18; 260/556 A; 260/566 F; 260/570.5 C; 260/570.8 R; 260/592; 424/316; 424/321; 424/330

[51] Int. Cl.² ........................................ C07C 91/16
[58] Field of Search............ 260/501.18, 254, 570.6

[56] References Cited
UNITED STATES PATENTS

| | | | |
|---|---|---|---|
| 3,135,797 | 6/1964 | Biel................................ | 260/570.6 |
| 3,139,441 | 6/1964 | Biel................................ | 260/570.6 X |
| 3,341,593 | 9/1967 | Zeile et al....................... | 260/570.6 |
| 3,410,901 | 11/1968 | Kunz et al....................... | 260/570.6 |
| 3,410,944 | 11/1968 | Claussen et al................. | 260/570.6 X |
| 3,463,808 | 8/1969 | Bond et al...................... | 260/570.6 X |

OTHER PUBLICATIONS
Zikolova et al., "Chemical Abstracts," vol. 61, p. 9485, (1964).

*Primary Examiner*—R. V. Hines
*Attorney, Agent, or Firm*—Hammond & Littell

[57] ABSTRACT

Compounds of the formula

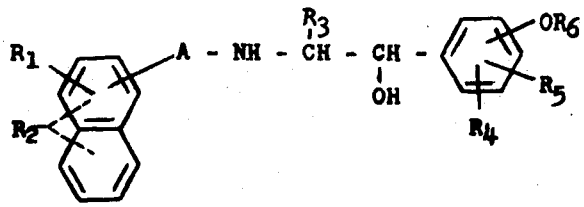

wherein
A is alkylene of 2 to 6 carbon atoms,
$R_1$ is hydrogen, lower alkyl, lower alkoxy, hydroxyl, or lower alkanoyloxy,
$R_2$ is hydrogen, lower alkyl or lower alkoxy,
$R_3$ is hydrogen, methyl or ethyl,
$R_4$ is hydrogen, lower alkyl or lower alkoxy,
$R_5$ is hydrogen, hydroxyl, lower alkanoyloxy or lower alkyl-sulfonamido, and
$R_6$ is hydrogen or lower alkanoyl,
and non-toxic, pharmacologically acceptable acid addition salts thereof; the compounds as well as their salts are useful as peripheral vasodilators, antihistaminics and spasmolytics.

7 Claims, No Drawings

1-PHENYL-2-(NAPHTHYLALKYL-AMINO)-ETHANOLS AND SALTS THEREOF

This is a continuation of Ser. No. 92,527 filed Nov. 24, 1970 and now abandoned.

This invention relates to novel 1-phenyl-2-(naphthylalkyl-amino)-ethanols and acid addition salts thereof, as well as to various methods of preparing these compounds.

More particularly, the present invention relates to racemic mixtures of compounds of the formula

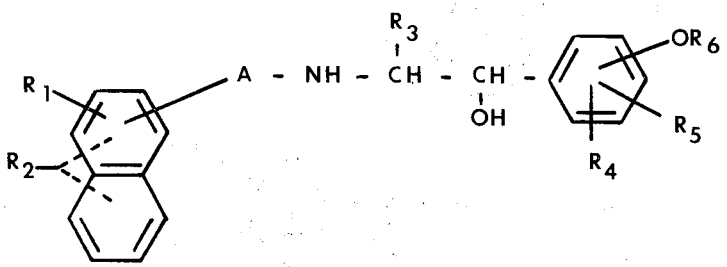

wherein
- A is alkylene of 2 to 6 carbon atoms,
- $R_1$ is hydrogen, lower alkyl, lower alkoxy, hydroxyl or lower alkanoyloxy,
- $R_2$ is hydrogen, lower alkyl or lower alkoxy,
- $R_3$ is hydrogen, methyl or ethyl,
- $R_4$ is hydrogen, lower alkyl or lower alkoxy,
- $R_5$ is hydrogen, hydroxyl, lower alkanoyloxy or lower alkyl-sulfonamido, and
- $R_6$ is hydrogen or lower alkanoyl, optically active antipode components thereof, and non-toxic, pharmacologically acceptable acid addition salts of said racemic mixtures or optically active antipodes.

The compounds of the formula I may be prepared by various methods involving known chemical principles, among which the following have proved to be particularly convenient and efficient:

METHOD A

By reducing an aminoketone of the formula

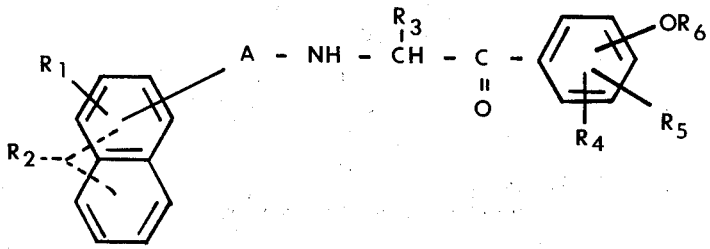

wherein A and $R_1$ through $R_6$ have the same meanings as in formula I. The reduction may be effected in a suitable inert solvent with hydrogen and a hydrogenation catalyst, such as Raney nickel, platinum or palladium; or with a complex hydride, such as sodium boranate; or by the Meerwein-Ponndorf Reduction [Annalen 444, 221 (1925); and Angew. Chem. 39, 138 (1926)].

The required starting compounds of the formula II may be prepared by reacting an amine of the formula

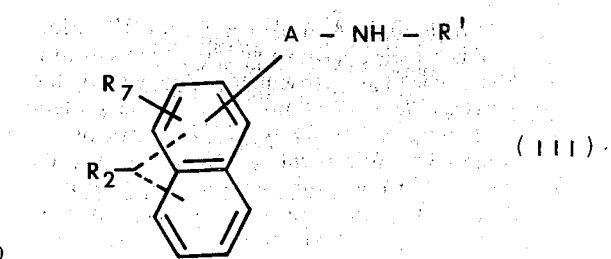

wherein
- A and $R_2$ have the same meanings as in formula I,
- R' is hydrogen of a substituent capable of being split off by hydrogenation, preferably arylmethyl and especially benzyl, and
- $R_7$ is hydrogen, lower alkyl, lower alkoxy or —OR", as hereinafter defined, with a compound of the formula

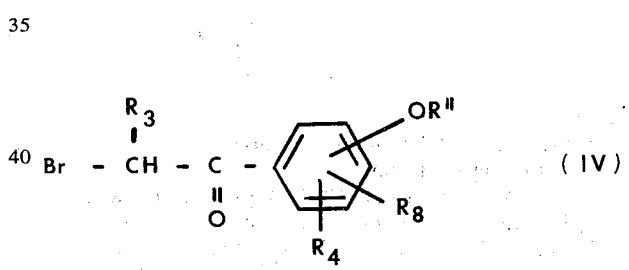

wherein
- $R_3$ and $R_4$ have the same meanings as in formula I,
- $R_8$ is hydrogen, lower alkyl-sulfonamido (lower alkyl-$SO_2$—NH—) or —OR", as hereinafter defined, and
- R" has the same meanings as $R_6$ in formula I or is an easily removable protective substituent, such as acyl, methyl or benzyl, or when —OR" and $R_8$ are in o-position with respect to each other, together diarylmethylene. In those instances where R' in formula III is other than hydrogen and R″ in formula IV is a readily removable protective substituent, these groups are subsequently removed by the appropriate conventional procedure. Thus, protective acyl substituents are removed by hydrolysis, are arylmethyl substituent on the nitrogen atom and diarylmethylene groups are removed by hydrogenation or by hydrolysis with an acid, such as hydrochloric acid or hydrobromic acid; and methyl substituents are removed by boiling with hydrobromic or hydroiodic acid.

Starting compounds of the formula II wherein A is straight or branched alkylene and $R_3$ is hydrogen, i.e. compounds of the formula

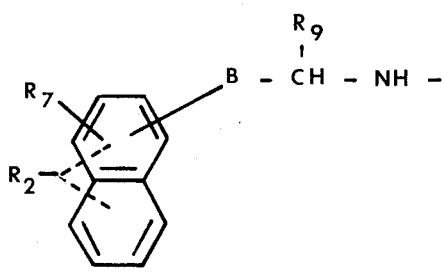

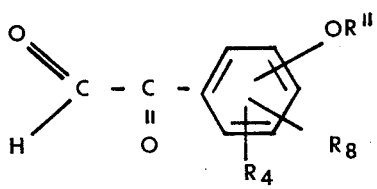 (V)

wherein
B is alkylene of 1 to 4 carbon atoms,
$R_9$ is hydrogen or methyl,
$R_2$ and $R_4$ have the same meanings as in formula I,
$R_7$ has the same meanings as in formula III, and
R″ and $R_8$ have the same meanings as in formula IV,
are prepared by reacting a compound of the formula

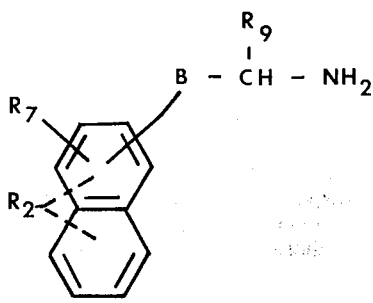 (VI)

wherein $R_4$, $R_8$ and R″ have the meanings previously defined, with an amine of the formula

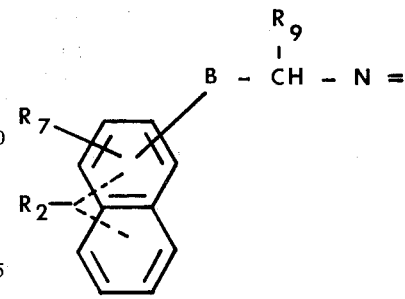 (VII)

wherein B, $R_2$, $R_7$ and $R_9$ have the meanings previously defined, under reductive amination conditions, or by hydrogenating a Schiff's base of the formula

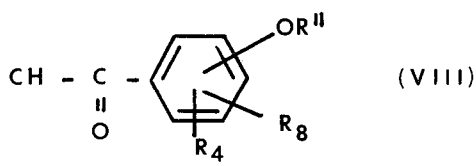

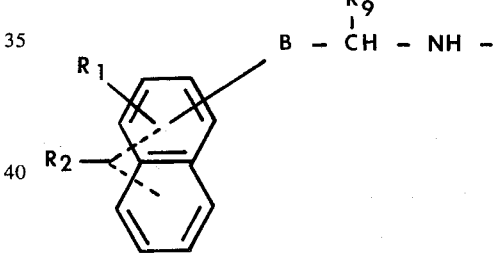 (VIII)

wherein B, R″, $R_2$, $R_4$, $R_7$, $R_8$ and $R_9$ have the meanings previously defined, and, if R″ is other than hydroxyl or lower alkanoyl, removing the same as described above.

METHOD B

For the preparation of a 1-phenyl-2-(naphthylalkyl-amino)-ethanol of the invention having the formula

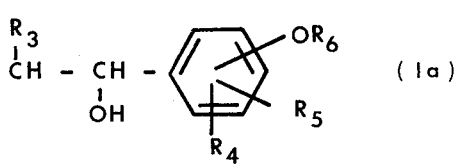

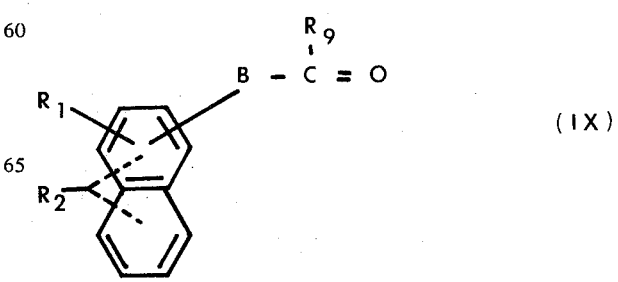 (Ia)

wherein
$R_1$ through $R_6$ have the same meanings as in formula I,
B is alkylene of 1 to 4 carbon atoms, and
$R_9$ is hydrogen or methyl,
by reacting an oxo-compound of the formula (IX)

wherein $R_1$, $R_2$, $R_9$ and B have the meanings previously defined, with an amine of the formula

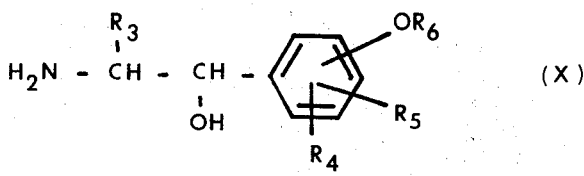

wherein $R_3$ through $R_6$ have the meanings previously defined, under reductive amination conditions, using conventional reducing agents; for example, hydrogen in the presence of a hydrogenation catalyst, such as Raney nickel, platinum or palladium, or a complex hydride, such as sodium boranate.

The starting compounds for this method are known compounds or may be prepared by conventional methods. For instance, an amine of the formula X may be prepared by way of a corresponding isonitrosoketone, cyanohydrin, benzoylcyanide and azidoketone. However, it is not necessary to first prepare and isolate the free amine; instead, the indicated compounds may, as such, be subjected to the reductive amination.

METHOD C

By removing the substituents to be removed from a compound of the formula

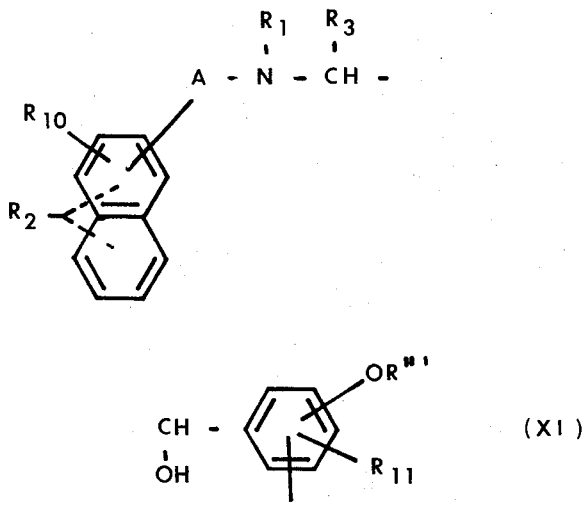

wherein
  $R_2$, $R_3$, $R_4$ and A have the same manings as in formula I,
  R' has the same meanings as in formula III,
  $R_{10}$ is hydrogen, lower alkyl, lower alkoxy or —OR''', as hereinafter defined.
  $R_{11}$ is hydrogen, lower alkyl-sulfonamido or —OR''', as hereinafter defined,
  R''' is hydrogen, lower alkanoyl, arylmethyl or aroyl, and,
if $R_{11}$ is the same as —OR''' and the two substituents are in o-position with respect to each other, the two R''' groups together are diarylmethylene, and at least one of R' and R''' is a substituent to be removed.

If both R' and R''' in the starting compound XI are substituents to be removed, the are removed simultaneously or successively, depending on the type, in accordance with conventional methods, and the reaction simultaneously converts $R_{10}$ into $R_1$, and $R_{11}$ into $R_5$.

As in method A, an arylmethyl substituent attached to the nitrogen is removed by hydrogenation; and arylmethyl or diarylmethylene substituent attached to oxygen is removed by hydrogenation or hydrolysis with an acid, such as hydrochloric or hydrobromic acid; and methyl substituents are removed by boiling with hydrobromic or hydroiodic acid.

The starting compounds of the formula XI may be prepared by reducing an aminoketone of the formula

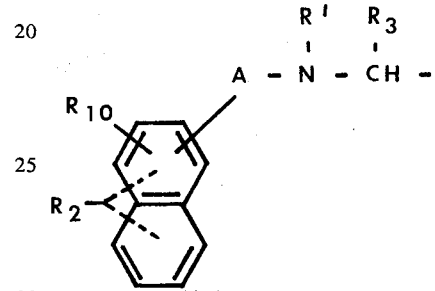

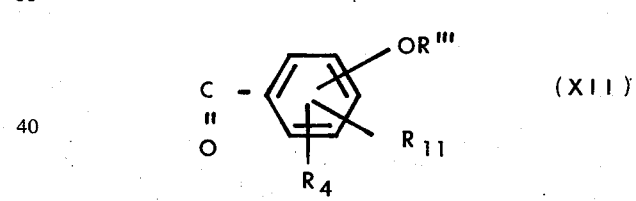

wherein $R_2$, $R_3$, $R_4$, $R_{10}$, $R_{11}$, R', R''' and A have the same meanings as in formula XI, into the corresponding alcohol; or by reacting an epoxide of the formula

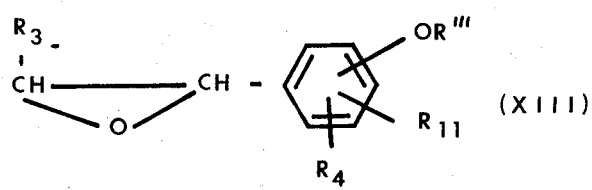

wherein $R_3$, $R_4$, $R_{11}$ and R''' have the meanings previously defined, with an amine of the formula

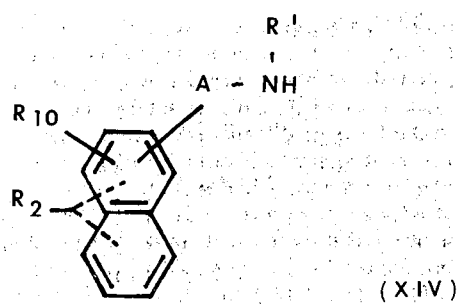

wherein R', R₂, R₁₀ and A have the meanings previously defined; or by reacting an amine of the formula XIV with a chlorohydrin of the formula

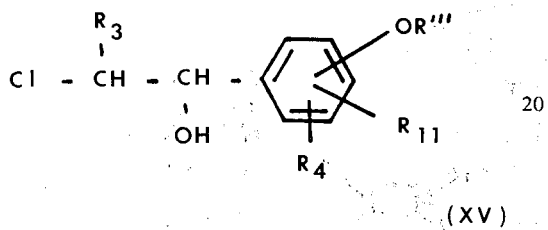

wherein R₃, R₄, R₁₁ and R''' have the meanings previously defined; or by alkylating an amine of the formula

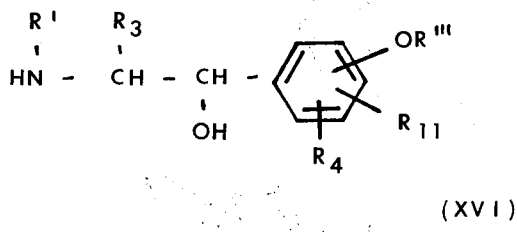

wherein R₃, R₄, R₁₁, R' and R''' have the meanings previously defined, with a compound of the formula

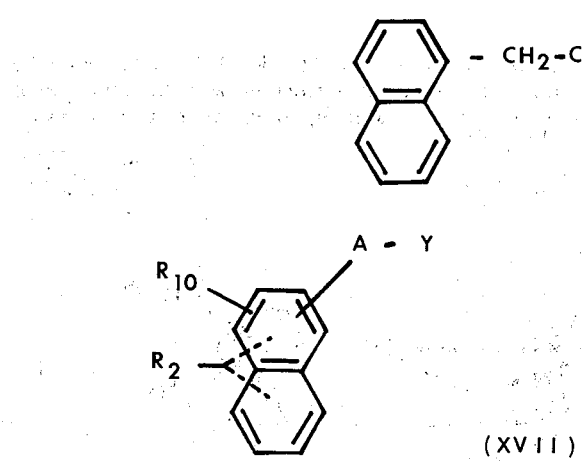

wherein R₂, R₁₀ and A have the meanings previously defined and Y is chlorine, bromine, iodine, lower alkylsulfonyl or arylsulfonyl.

A racemic mixture of a compound of the formula I obtained by methods A to C above may, if desired, be resolved into its optically active antipode components by conventional methods.

Likewise, since the compounds of the formula I are bases, the racemates as well as the optically active antipodes form acid addition salts with inorganic or organic acids, and may, if desired, be converted into such salts by conventional methods. Examples of non-toxic, pharmacologically acceptable acid addition salts are those formed with hydrochloric acid, hydrobromic acid, sulfuric acid, nitric acid, phosphoric acid, citric acid, tartaric acid, maleic acid, salicylic acid, 8-chloro-theophylline or the like.

The following examples further illustrate the present invention and will enable others skilled in the art to understand it more completely. It should be understood, however, that the invention is not limited solely to the particular examples given below.

EXAMPLE 1

1-(2'-Methoxy-3',4'-dihydroxy-phenyl)-2-[2''-methyl-4''-(1'''-naphthyl)-2''-butyl-amino]-ethanol hydrochloride by method A A mixture consisting of 38.5 gm of 2-bromo-3,4-diphenylmethylenedihydroxy-acetophenone (m.p. 136°–138°C), 29 gm of 4-(1'-naphthyl)-2-methyl-2-butyl-amine (b.p. 187°–190°C at 12 mm Hg), 10 gm of sodium carbonate and 100 ml of ethanol was refluxed for 3 hours. Thereafter, the reaction mixture was vacuum-filtered, the filtrate was acidified with concentrated hydrochloric acid, 100 ml of water were added, and the precipitate formed thereby, α-[2'-methyl-4'-(1''-naphthyl)-2'-butyl-amino]-2-methoxy-3,4-diphenyl-methylenedihydroxy-acetophenone hydrochloride (m.p. 195°–200°C), was collected by vacuum filtration. The filter cake was boiled for 2 hours with aqueous 15% hydrochloric acid, yielding α-[2'-methyl-4'-(1''-naphthyl)-2'-butyl-amino]-2-methoxy-3,4-dihydroxy-acetophenone hydrochloride (m.p. 116°–120°C) which, in turn, was hydrogenated by catalytic hydrogenation in methanol under standard conditions with platinum as the catalyst, yielding the compound of the formula

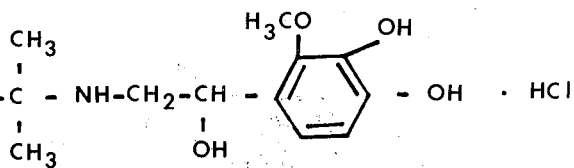

having a melting point of 120°–124°C.

EXAMPLE 2

1-(4'-Hydroxy-phenyl)-2-[2''-(1'''-naphthyl)-ethyl-amino]-ethanol by method A

A mixture consisting of 45.75 gm of α-bromo-4-benzyloxy-acetophenone, 78 gm of N-[2-(1'-naphthyl)-ethyl]-benzylamine and 250 ml of acetonitrile was refluxed for 1 hour. Thereafter, the precipitate formed thereby was filtered off, and the filtrate was evaporated. The residue was subjected to catalytic hydrogenation in methanol in the presence of hydrochloric acid and palladized charcoal, yielding α-[2'-(1''-naphthyl)-ethyl-amino]-4-hydroxy-acetophenone hydrochloride (m.p. 171°–177°C), from which the free base (m.p. 166°C) was liberated by addition of aqueous ammonia.

The free base was subjected to catalytic hydrogenation with Raney nickel in methanol under standard conditions, yielding the compound of the formula

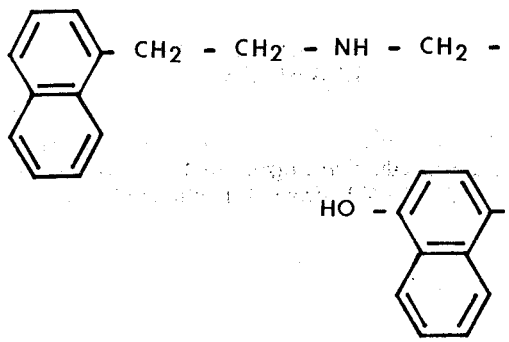

having a melting point of 143°–146°C.

EXAMPLE 3

1-(3',5'-Dihydroxy-phenyl)-2-[2''-(4''''-hydroxy-1'''-naphthyl)-ethyl-amino]-ethanol hydrobromide by method A A mixture consisting of 31.5 gm of α-bromo-3,5-diacetoxy-acetophenone, 58.2 gm of N-[2-(4'-methoxy-1'-naphthyl)-ethyl]-benzylamine and 200 ml of acetonitrile was refluxed for 30 minutes. Thereafter, the precipitate formed thereby was separated by vacuum filtration, and the filtrate was evaporated. The residue was dissolved in 300 ml of methanol, the resulting solution was acidified with ethereal hydrochloric acid, and the acidic solution was hydrogenated at 60°C and 5 atmospheres gauge in the presence of 15 ml PdCl₂/1.5 gm activated charcoal. Thereafter, the catalyst was filtered off, 100 ml of concentrated hydrochloric acid were added to the filtrate, and the acid solution was refluxed for 30 minutes. The precipitate formed thereby, α-[2'-(4''-methoxy-1''-naphthyl)-ethyl-amino]-3,5-dihydroxy-acetophenone hydrochloride (m.p. 242°C), was collected and boiled with aqueous 48% hydrobromic acid, yielding α-[2'-(4''-hydroxy-1''-naphthyl)-ethyl-amino]-3,5-dihydroxy-acetophenone hydrobromide which, upon recrystallization from water, had a melting point of 248°–252°C. This product was subjected to catalytic hydrogenation in methanol in the presence of platinum oxide under standard conditions, yielding the compound of the formula

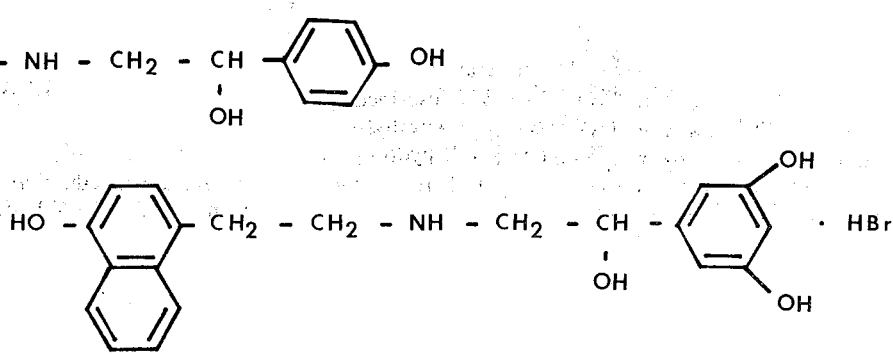

having a melting point of 222°C.

EXAMPLE 4

Using a procedure analogous to that described in Example 3, 1-(4'-hydroxy-phenyl)-2-[2'-methyl-4'-(1'''-naphthyl)-2-butyl-amino]-ethanol hydrochloride, m.p. 197°C (decomp.), of the formula

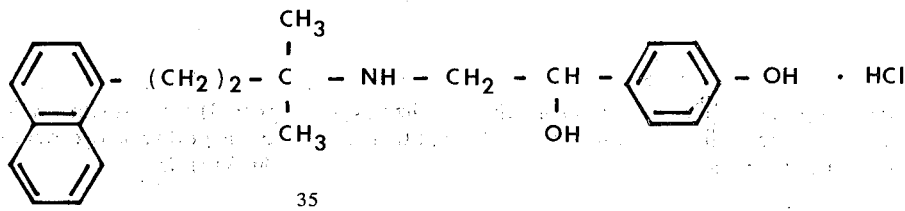

was prepared from α-bromo-4-acetoxy-acetophenone and N-[2-methyl-4-(1'-naphthyl)-2-butyl]-amine.

EXAMPLE 5

Using a procedure analogous to that described in Example 3, 1-(4'-hydroxy-phenyl)-2-[2'-(4''-hydroxy-1''-naphthyl)-ethyl-amino]-ethanol hydrochloride with one molecule of water of crystallization, m.p. 97°C, of the formula

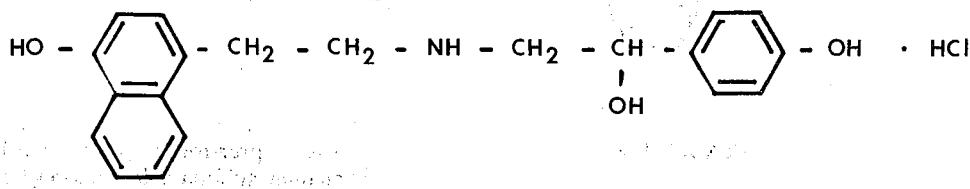

was prepared from α-bromo-4-benzyloxy-acetophenone and N-[2-(4'-methoxy-1'-naphthyl)-ethyl]-benzylamine.

EXAMPLE 6

Using a procedure analogous to that described in Example 2, 1-(4'-hydroxy-2'-methyl-phenyl)-2-[2''-methyl-4''-(1''''-naphthyl)-2-butyl-amino]-ethanol, m.p. 150°C, and its hydrochloride, m.p. 176°–177°C, of the formula

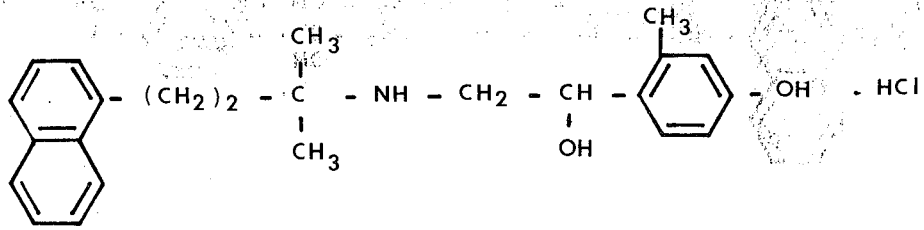

was prepared from α-bromo-2-methyl-4-benzyloxy-acetophenone and N-[2-methyl-4-(1'-naphthyl)-2-butyl]-benzylamine.

EXAMPLE 7

Using a procedure analogous to that described in Example 2, 1-(4'-hydroxy-phenyl)-2-[2''-methyl-4''-(1'''-naphthyl)-2''-butyl-amino]-propanol hydrochloride, m.p. 227°C, of the formula

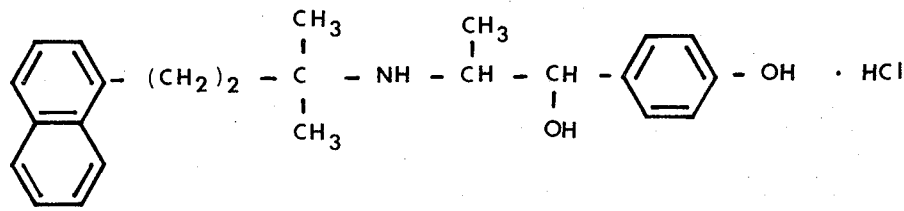

was prepared from α-bromo-α-methyl-4-benzyloxy-acetophenone and N-[2-methyl-4-(1'-naphthyl)-2-butyl]-benzylamine.

EXAMPLE 8

Using a procedure analogous to that described in Example 3, 1-(3',4'-dihydroxy-phenyl)-2-[2''-(4''-hydroxy-1'-naphthyl)-ethyl-amino]-ethanol hydrobromide, m.p. 167°–169°C, of the formula was prepared from α-bromo-3,4-diacetoxy-acetophenone and N-[2-(4'-hydroxy-1'-naphthyl)-ethyl]-benzylamine.

EXAMPLE 9

Using a procedure analogous to that described in Example 2, 1-(4'-hydroxy-3'-methanesulfonamido-phenyl)-2-[2''-methyl-4''-(1'''-naphthyl)-2-butyl-amino]-ethanol hydrochloride, m.p. 199°–201°–C, of the formula

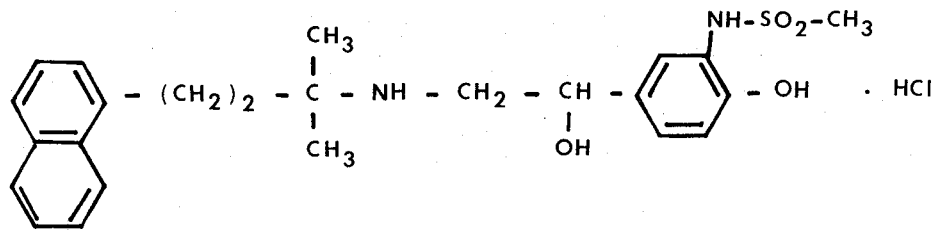

was prepared from α-bromo-4-benzyloxy-3-methanesulfonamido-acetophenone and N-[2-methyl-4-(1'-naphthyl)-2-butyl]-benzylamine.

EXAMPLE 10

Using a procedure analogous to that described in

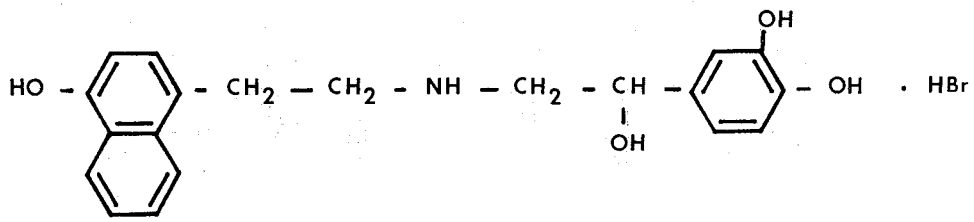

Example 2, 1-(4'-hydroxy-phenyl)-2-[2''-methyl-4''-(2'''-naphthyl)-2''-butyl-amino]-ethanol, m.p. 153°–156°C, of the formula

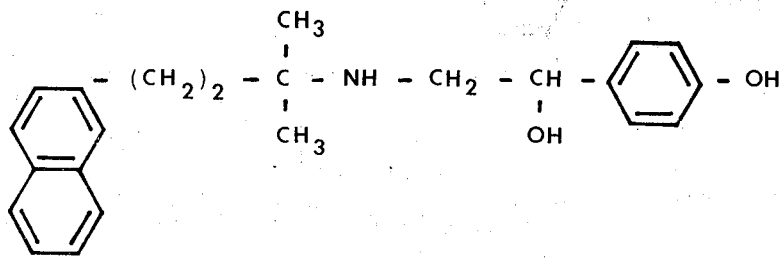

was prepared from α-bromo-4-benzyloxy-acetophenone and N-[2-methyl-(2'-naphthyl)-2butyl]-benzylamine.

EXAMPLE 11

Using a procedure analogous to that described in Example 2, 1-(4'-hydroxy-phenyl)-2-[2''-methyl-4''-(2'''-methyl-1'''-naphthyl)-2''-butyl-amino]-ethanol, m.p. 188°C, and its hydrochloride, m.p. 168°–170°C, of the formula

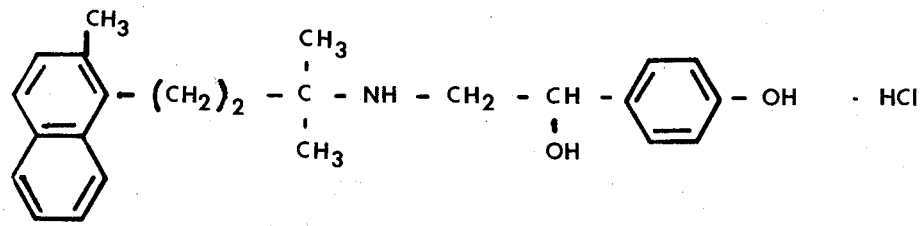

was prepared from α-bromo-4-benzyloxy-acetophenone and N-[2-methyl-4-(2'-methyl-1'-naphthyl)-2-butyl]-benzylamine.

EXAMPLE 12

Using a procedure analogous to that described in Example 1, 1-(2'-methoxy-3',4'-dihydroxy-phenyl)-2-[2''-methyl-4''-(2'''-methyl-1'''-naphthyl)-2''-butyl-amino]-ethanol hydrochloride, m.p. 143°C (decomp.), of the formula

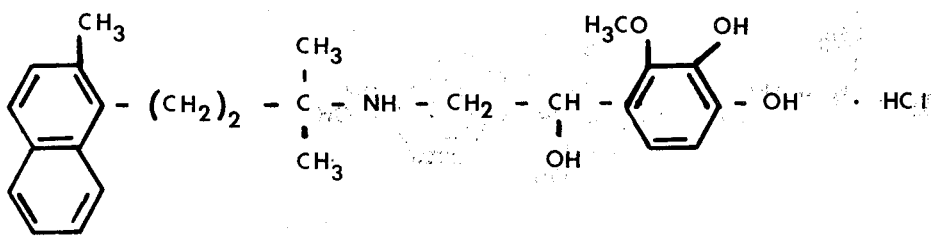

was prepared from α-bromo-3,4-diphenylmethylenedioxy-acetophenone and 4-(1-naphthyl)-2-methyl-2-butylamine.

EXAMPLE 13

Using a procedure analogous to that described in Example 1, 1-(4'-acetoxy-phenyl)-2-[2''-methyl-4''-(1'''-naphthyl)-2''-butyl-amino]-ethanol hydrochloride, m.p. 179°–182°C, of the formula

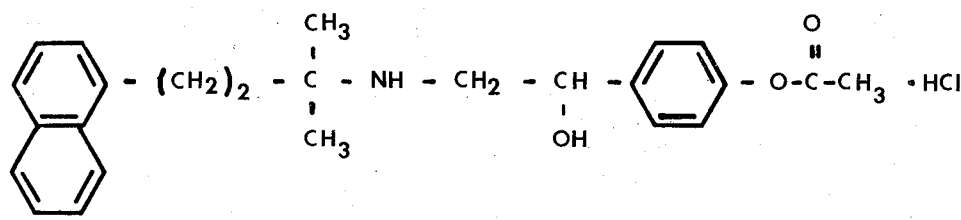

was prepared from α-bromo-4-acetoxy-acetophenone and 4-(1'-naphthyl)-2-methyl-2-butylamine.

EXAMPLE 14

Using a procedure analogous to that described in Example 3, 1-(3',5'-dihydroxy-phenyl)-2-[4''-(1'''-naphthyl)-2''-butyl-amino]-ethanol, m.p. 166°–169°C, of the formula

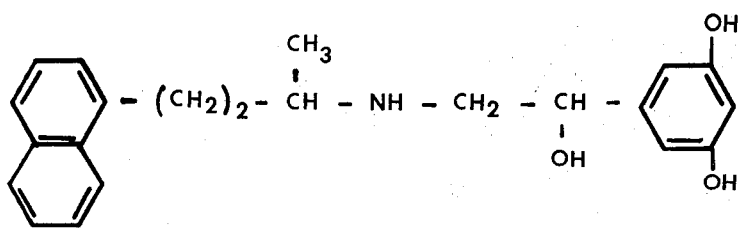
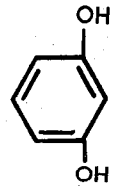

was prepared from α-bromo-3,5-diacetoxy-acetophenone and N-[4-(1'-naphthyl)-2-butyl]-benzylamine.

EXAMPLE 15

Using a procedure analogous to that described in Example 3, 1-(4'-hydroxy-phenyl)-2-[1'''-(4''''-hydroxy-1''''-naphthyl)-2''-propyl-amino]-ethanol hydrochloride, m.p. 199°–202°C, of the formula

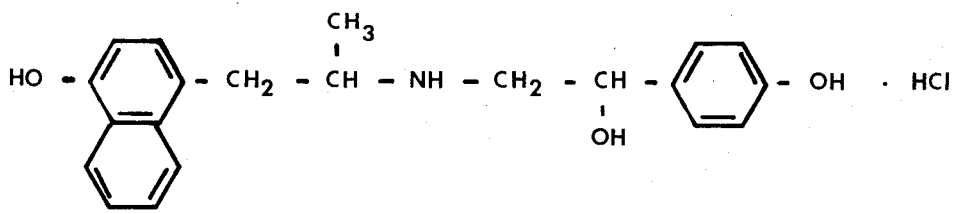

was prepared from α-bromo-4-benzyloxy-acetophenone and N-[1-(4'-methoxy-1'-naphthyl)-2-propyl]-benzylamine.

EXAMPLE 16

Using a procedure analogous to that described in Example 1, 1-(4'-hydroxy-phenyl)-2-[1'''-(4''''-methoxy-1''''-naphthyl)-2''-propyl-amino]-ethanol, m.p. 190°–192°C, of the formula was prepared from α-bromo-4-benzyloxy-acetophenone and N-[1-(4'-methoxy-1'-naphthyl)-2-propyl]-benzylamine.

EXAMPLE 17

Using a procedure analogous to that described in Example 1, 1-(4'-hydroxy-phenyl)-2-[2''-(4''''-methyl-1''''-naphthyl)-ethyl-amino]-ethanol hydrochloride, m.p. 162°C, of the formula

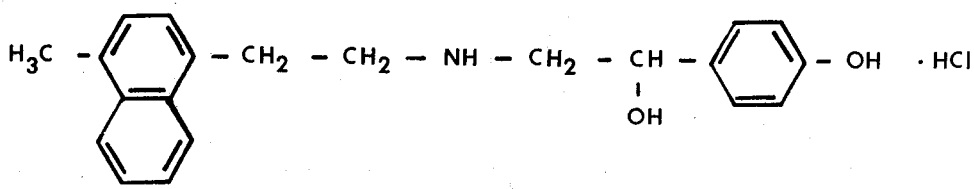

was prepared from α-bromo-4-benzyloxy-acetophenone and N-[2-(4'-methyl-1'-naphthyl)-ethyl]-benzylamine.

EXAMPLE 18

Using a procedure analogous to that described in Example 1, 1-(3'-hydroxy-phenyl)-2-[2''-(4''''-methoxy-1''''-naphthyl)-ethyl-amino]-ethanol hydrochloride, m.p. 142°–144°C, of the formula

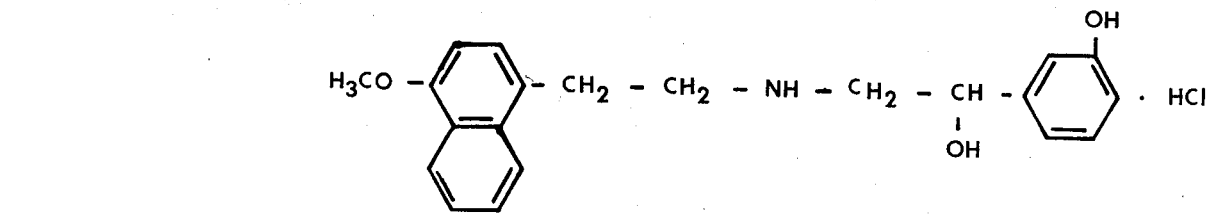

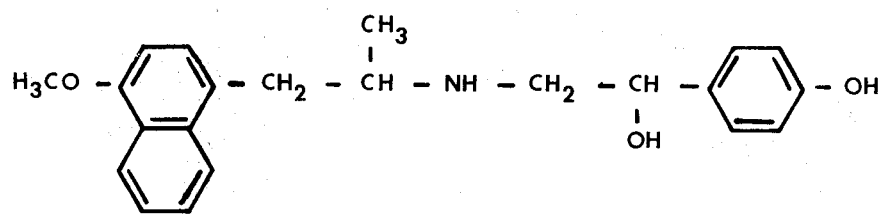

was prepared from α-bromo-3-benzyloxy-acetophenone and N-[2-(4'-methoxy-1'-naphthyl)-ethyl]-benzylamine.

EXAMPLE 19

Using a procedure analogous to that described in Example 1, 1-(2'-methyl-3',4'-dihydroxy-phenyl)-2-[2''-methyl-4''-(1''''-naphthyl)-2''-butyl-amino]-ethanol, m.p. 175°–177°C, and its hydrochloride, m.p. 145°–148°C, of the formula

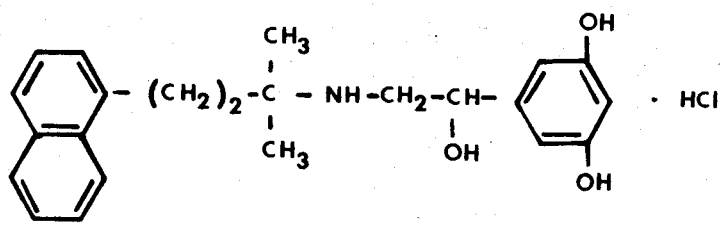

was prepared from α-bromo-2-methyl-3,4-diphenyl-methylene-dioxy-acetophenone and 4-(1'-naphthyl)-2-methyl-2-butylamine.

EXAMPLE 20

Using a procedure analogous to that described in Example 3, 1-(3',5'-dihydroxy-phenyl)-2-[2''-methyl-4''-(1''''-naphthyl)-2''-butyl-amino]-ethanol, m.p. 117°–118°C, and its hydrochloride, m.p. 135°–140°C, of the formula

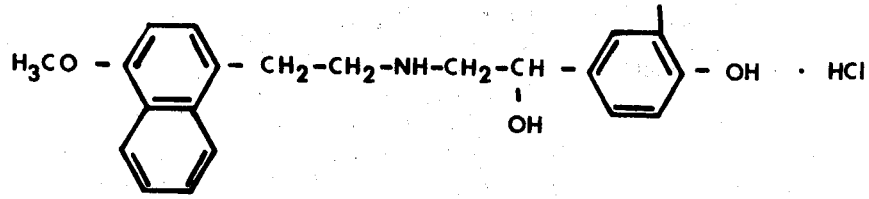

was prepared from α-bromo-3,5-diacetoxy-acetophenone and N-[2-methyl-4-(1''-naphthyl)-2-butyl]-benzylamine.

EXAMPLE 21

Using a procedure analogous to that described in Example 1, 1-(3',4'-dihydroxy-phenyl)-2-[2''-(4'''-methoxy-1'''-naphthyl)-ethyl-amino]-ethanol hydrochloride, m.p. 195°–196°C, of the formula

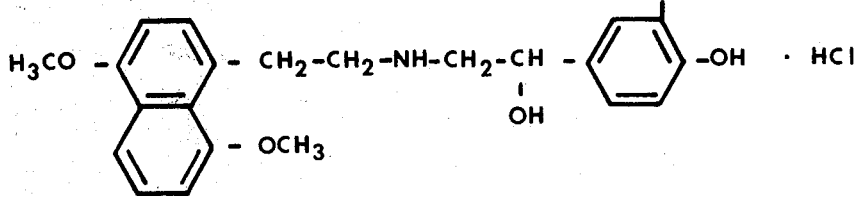

was prepared from α-bromo-3,4-diphenylmethylene-dioxy-acetophenone and 2-(4'-methoxy-1'-naphthyl)-ethylamine.

EXAMPLE 22

Using a procedure analogous to that described in Example 2, 1-(4'-hydroxy-phenyl)-2-[2''-methyl-1''-(1''''-naphthyl)-2''-propyl-amino]-ethanol, m.p. 153°–156°C, of the formula

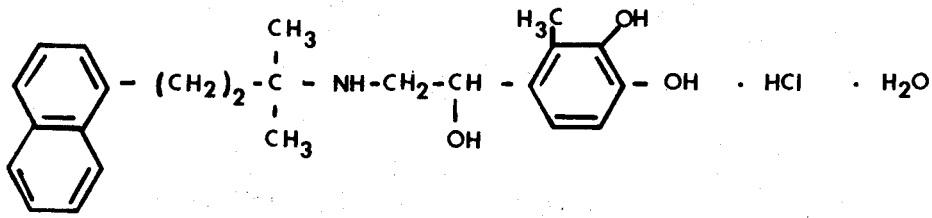

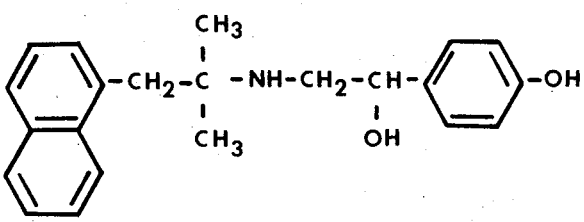

was prepared from α-bromo-4-benzyloxy-acetophenone and N-[2-methyl-1-(1'-naphthyl)-2-propyl]-benzylamine.

EXAMPLE 23

Using a procedure analogous to that described in Example 1, 1-(3',4'-dihydroxy-phenyl)-2-[2''-(4''',8'λ''-dimethoxy-1'''-naphthyl)-ethyl-amino]-ethanol hydrochloride, m.p. 198°–199°C, of the formula

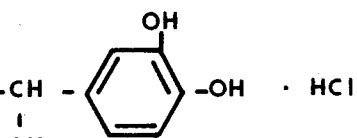

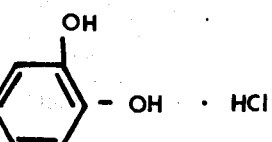

was prepared from α-bromo-3,4-diphenylmethylenedioxy-acetophenone and 2-(4',8'-dimethoxy-1'-naphthyl)-ethylamine.

EXAMPLE 24

1-(3',5'-Dihydroxy-phenyl)-2-[4''-(1'''-naphthyl)-2''-butylamino]-ethanol by method B A mixture consisting of 8.5 gm of 1-(3',5'-dihydroxyphenyl)-2-amino-ethanol, 10 gm of 1-(4'-naphthyl)-2-butanone, 6 gm of glacial acetic acid, 200 ml of methanol and 4 gm of platinum oxide was hydrogenated under standard conditions until absorption of hydrogen was complete. Thereafter, the catalyst was filtered off, and the filtrate was evaporated. The residue was dissolved in 100 ml of water, and the resulting solution was acidified with concentrated hydrochloric acid and then extracted twice with ether, the ether extracts being discarded. The aqueous phase was made alkaline with aqueous ammonia and then extracted twice with 100 ml of ethyl acetate. The extract solutions were combined, dried with sodium sulfate and evaporated. The residue was treated with acetonitrile and yielded the same compound as in Example 14, m.p. 166°–169°C.

EXAMPLE 25

1-(4'-Hydroxy-phenyl)-2-[1''-(4'''-hydroxy-1'''-naphthyl)-2''-propyl-amino]-ethanol and its hydrochloride by method B A mixture consisting of 7.65 gm of 1-(4'-hydroxyphenyl)-2-amino-ethanol, 10 gm of 2-(4'-hydroxy-1'-naphthyl)-propanone-(2), 6 gm of glacial acetic acid, 4 gm of platinum oxide and 200 ml of methanol was hydrogenated under standard conditions until absorption of hydrogen was complete. Thereafter, the catalyst was filtered off, the filtrate was evaporated, the residue was admixed with water and aqueous ammonia, and the aqueous mixture was extracted twice with ethyl acetate. The extract solutions were combined, dried over sodium sulfate and evaporated, yielding the free base 1-(4'-hydroxy-phenyl)-2-[1''-(4'''-hydroxy-1'''-naphthyl)-2''-propyl-amino]-ethanol, which was converted into its hydrochloride m.p. 199°–202°C, with aqueous hydrochloric acid, resulting in the same compound as in Example 15.

EXAMPLE 26

Using a procedure analogous to that described in Example 25, 1-(4'-hydroxy-phenyl)-2-[1''-(4'''-methoxy-1'''-naphthyl)-2''-propyl-amino]-ethanol, m.p. 190°–192°C, was prepared from 1-(p-hydroxyphenyl)-2-amino-ethanol and 2-(4'-methoxy-1'-naphthyl)-acetone.

EXAMPLE 27

Using a procedure analogous to that described in Example 25, 1-(4'-hydroxy-phenyl)-2-[2''-(4'''-methyl-1'''-naphthyl)-ethyl-amino]-ethanol hydrochloride, m.p. 162°C, was prepared from 1-(4'-hydroxy-phenyl)-2-amino-ethanol and 2-(4'-hydroxy-1'-naphthyl)-propanone-(2).

EXAMPLE 28

Using a procedure analogous to that described in Example 25, 1-(3'-hydroxy-phenyl)-2-[2''-(4'''-methoxy-1'''-naphthyl)-ethyl-amino]-ethanol hydrochloride, m.p. 142°–144°C, was prepared from 1-(3'-hydroxy-phenyl)-2-amino-ethanol and 2-(4'-methoxy-1'-naphthyl)-acetone.

EXAMPLE 29

Using a procedure analogous to that described in Example 25, 1-(4'-hydroxy-phenyl)-2-[2''-(4'''-hydroxy-1'''-naphthyl)-ethyl-amino]-ethanol hydrochloride with 1 mol of water of crystallization, m.p. 97°C, was prepared from 1-(4'-hydroxy-phenyl)-2-amino-ethanol and 2-(4'-hydroxy-1'-naphthyl)-acetone.

EXAMPLE 30

Using a procedure analogous to that described in Example 24, 1-(3',4'-dihydroxy-phenyl)-2-[2''-(4'''-methoxy-1'''-naphthyl)-ethyl-amino]-ethanol hydrochloride, m.p. 195°–196°C, was prepared from 1-(3',4'-dihydroxy-phenyl)-2-amino-ethanol and 2-(4'-methoxy-1'-naphthyl)-acetone.

EXAMPLE 31

Using a procedure analogous to that described in Example 24, 1-(3',4'-dihydroxy-phenyl)-2-[2''-(4'''-hydroxy-1'''-naphthyl)-ethyl-amino]-ethanol hydrobromide, m.p. 167°–169°C, was prepared from 1-(3',4'-dihydroxy-phenyl)-2-amino-ethanol and 2-(4'-hydroxy-1'-napthyl)-acetone.

EXAMPLE 32

Using a procedure analogous to that described in Example 24, 1-(3',4'-dihydroxy-phenyl)-2-[2''-(4''',8'''-dimethoxy-1'''-naphthyl)-ethyl-amino]-ethanol hydrochloride, m.p. 198°–199°C, was prepared from 1-(3',4'-dihydroxy-phenyl)-2-amino-ethanol and 2-(4',8'-dimethoxy-1'-naphthyl)-acetone.

EXAMPLE 33

Using a procedure analogous to that described in Example 25, 1-(4'-hydroxy-phenyl)-2-[2''-(1'''-naphthyl)-ethyl-amino]-ethanol, m.p. 143°–146°C, was prepared from 1-(4'-hydroxy-phenyl)-2-amino-ethanol and 2-(1'-naphthyl)-acetone.

EXAMPLE 34

Using a procedure analogous to that described in Example 24, 1-(3',5'-dihydroxy-phenyl)-2-[2''-(4'''-hydroxy-1'''-naphthyl)-ethyl-amino]-ethanol hydrobromide, m.p. 222°C, was prepared from 1-(3',5'-dihydroxy-phenyl)-2-amino-ethanol and 2-(4'-hydroxy-1'-naphthyl)-acetone.

EXAMPLE 35

1-(4'-Hydroxy-phenyl)-2-[2''-methyl-4''-(1'''-naphthyl)-2''-butyl-amino]-ethanol by method A A mixture consisting of 30.5 gm of α-bromo-p-benzyloxy-acetophenone (m.p. 78°C), 27.5 gm of 4-(1'-naphthyl)-2-methyl-2-butylamine, 11 gm of sodium bicarbonate and 200 ml of ethanol was refluxed for 3 hours. Thereafter, the reaction mixture was filtered, the filtrate was acidified with concentrated hydrochloric acid, and the acidic solution was diluted with water, whereupon α-[2'-methyl-4'-(1''-naphthyl)-2'-butylamino]-4-benzyloxy-acetophenone hydrochloride (m.p. 200°–205°C) precipitated out. The corresponding free base, liberated from the hydrochloride with aqueous ammonia, was then reduced with sodium borohydride in 200 ml of ethanol to form 1-(4'-benzyloxy-phenyl)-2-[2''-methyl-4''-(1'''-naphthyl)-2''-butyl-amino]-ethanol (m.p. 123°–125°C), which in turn was subjected to catalytic hydrogenation with Raney nickel catalytic hydrogenation in methanol at 60°C and 5 atmospheres gauge with palladized charcoal as the catalyst; yielding 1-(2'-methyl-3',4'-dihydroxy-phenyl)-2-[2''-methyl-4''-(1'''-naphthyl)-2''-butyl-amino]-ethanol, m.p. 175°–177°C, of the formula

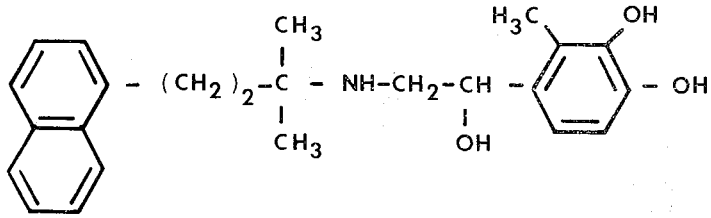

in methanol, yielding 1-(4'-hydroxy-phenyl)-2-[2''-methyl-4''-(1'''-naphthyl)-2''-butyl-amino]-ethanol.

Its hydrochloride had a melting point of 197°C (decomp.).

EXAMPLE 36

1-(3'-Methansulfonamido-4'-hydroxy-phenyl)-1-[2''-methyl-4''-(1'''-naphthyl)-2''-butyl-amino]-ethanol by method A A mixture consisting of 40 gm of α-bromo-3-methanesulfonamido-4-benzyloxy-acetophenone (m.p. 119°C), 41.6 gm of 4-(1'-naphthyl)-2-methyl-2-benzyl-2-butyl-amine and 300 ml of benzene was stirred for 1 hour at room temperature. Thereafter, the precipitate formed thereby was separated by vacuum filtration, the benzene was distilled out of the filtrate, the residue was dissolved in ethyl acetate, and the resulting solution was acidified with ethereal hydrochloric acid, whereupon α-[2'-methyl-4'-(1'''-naphthyl)-2'-butyl-amino]-3-methanesulfonamido-4-benzyloxy-acetophenone hydrochloride (m.p. 155°–158°C) crystallized out. The corresponding free base, liberated therefrom with aqueous ammonia, was reduced with sodium borohydride in methanol in the presence of the calculated amount of 1 N sodium hydroxide, and the reduction product was subjected to catalytic hydrogenation in methanol under standard conditions with palladized charcoal as the catalyst. 1-(3'-methanesulfonamido-4'-hydroxyphenyl)-2-[2''-methyl-4''-(1'''-naphthyl)-2''-butylamino]-ethanol, m.p. 175°–179°C, was obtained.

Its hydrochloride, prepared from the free base with ethereal hydrochloric acid, had a melting point of 199°–201°C.

EXAMPLE 37

1-(2'-Methyl-3',4'-dihydroxy-phenyl)-2-[2''-methyl-4''-(1'''-naphthyl)-2''-butyl-amino]-ethanol by method A A mixture consisting of 30 gm of α-bromo-2-methyl-3,4-dibenzyloxy-acetophenone (m.p. 128°–129°C), 23 gm of 4-(1'-naphthyl)-2-methyl-2-butylamine, 10 gm of sodium carbonate and 100 ml of ethanol was refluxed for 3 hours. Thereafter, the reaction mixture was vacuum-filtered, the filtrate was acidified with concentrated hydrochloric acid, the acidic solution was diluted with water, and the precipitated α-[2'-methyl-4'-(1''-naphthyl)-2'-butyl-amino]-2-methyl-3,4-dibenzyloxy-acetophenone hydrochloride (m.p. 140°–145°C) was collected by vacuum filtration. The free base, liberated from the hydrochloride with aqueous ammonia, was reduced with sodium borohydride in ethanol, and the reduction product was subjected to Its hydrochloride with 1 mol of water of crystallization, prepared by dissolving the free base in water and acidifying the solution with hydrochloric acid, had a melting point of 145°–148°C.

EXAMPLE 38

1-(3',5'-Dihydroxy-phenyl)-2-[2''-methyl-4''-(1'''-naphthyl)-2''-butyl-amino]-ethanol by method A A mixture consisting of α-bromo-3,5-dibenzyloxy-acetophenone (obtained by brominating 25 gm of 3,5-dibenzyloxy-acetophenone), 15 gm of 4-(1'-naphthyl)-2-methyl-2-butylamine, 10 gm of sodium carbonate and 100 ml of acetonitrile was refluxed for 3 hours. Thereafter, the reaction mixture was vacuum-filtered, the filtrate was evaporated, the residue was dissolved in ethyl acetate, and the resulting solution was acidified with ethereal hydrochloric acid, whereupon α-[2'-methyl-4'-(1''-naphthyl)-2'-butyl-amino]-3,5-dibenzyloxy-acetophenone hydrochloride, (m.p. 165°–170°C) crystallized out. The free base, liberated from the hydrochloride with aqueous ammonia, was reduced in ethanol with sodium borohydride to form 1-(3',5'-dibenzyloxy-phenyl)-2-[2''-methyl-4''-(1'''-naphthyl)-2''-butyl-amino]-ethanol (m.p. 117°–118°C) which, in turn, was subjected to catalytic hydrogenation in methanol under standard conditions with Raney nickel as the catalyst, yielding 1-(3',5'-dihydroxy-phenyl-2-[2''-methyl-4''-(1''' -naphthyl)-2''-butyl-amino]-ethanol.

Its hydrochloride had a melting point of 135°–140°C.

EXAMPLE 39

Using a procedure analogous to that described in Example 35, 1-(4'-hydroxy-phenyl)-2-[2''-methyl-4''-(2'''-naphthyl)-2''-butyl-amino]-ethanol, m.p. 153°–156°C, prepared from α-bromo-4-benzyloxy-acetophenone and 4-(2'-naphthyl)-2-methyl-2-butyl-amine.

EXAMPLE 40

Using a procedure analogous to that described in Example 38, 1-(3',4'-dihydroxy-phenyl)-2-[2''-(4'''-methoxy-1'''-naphthyl)-ethyl-amino]-ethanol hydrochloride, m.p. 195°–196°C, was prepared from α-bromo-3,4-dibenzyloxy-acetophen-one and 2-(4'-methoxy-1'-naphthyl)-ethyl-amine.

EXAMPLE 41

Using a procedure analogous to that described in Example 38, 1-(2'-methoxy-3',4'-dihydroxy-phenyl)-2-[2''-methyl-4''-(1'''-naphthyl)-2''-butyl-amino]-ethanol hydrochloride, m.p. 120°–124°C, was prepared from α-bromo-2-methoxy-3,4-dibenzyloxy-acetophenone and 4-(1'-naphthyl)-2-methyl-2-butyl-amine.

EXAMPLE 42

Using a procedure analogous to that described in Example 35, 1-(4'-hydroxy-phenyl)-2-[2''-methyl-1''-(1''''-naphthyl)-2''-propyl-amino]-ethanol, m.p. 153°–156°C, was prepared from α-bromo-4-benzyloxy-acetophenone and 1-(1'-naphthyl)-2-methyl-2-propyl-amine.

EXAMPLE 43

Using a procedure analogous to that described in Example 35, 1-(4'-hydroxy-phenyl)-2-[2''-(4'''-hydroxy-1''''-naphthyl)-ethyl-amino]-ethanol hydrochloride with 1 mol of water of crystallization, m.p. 97°C, was prepared from α-bromo-4-benzyloxy-acetophenone and 2-(4'-hydroxy-1'-naphthyl)-ethyl-amine.

EXAMPLE 44

Using a procedure analogous to that described in Example 35, 1-(4'-hydroxy-phenyl)-2-[2''-methyl-4''-(1''''-naph-thyl)-2''-butyl-amino]-propanol hydrochloride, m.p. 227°C, was prepared from α-bromo-4-benzyloxy-propiophenone and 4-(1'-naphthyl)-2-methyl-2-butyl-amine.

EXAMPLE 45

Using a procedure analogous to that described in Example 39, 1-(3',4'-dihydroxy-phenyl)-2-[2''-(4''',8'''-dimethoxy-1''''-naphthyl)-ethyl-amino]-ethanol hydrochloride, m.p. 198°–199°C, was prepared from α-bromo-3,4-dibenzyloxy-acetophenone and 2-(4',8'-dimethoxy-1'-naphthyl)-ethyl-amine.

EXAMPLE 46

Using a procedure analogous to that described in Example 38, 1-(3',5'-dihydroxy-phenyl)-2-[2''-(4'''-hydroxy-1''''-naphthyl)-ethyl-amino]-ethanol hydrobromide, m.p. 222°C, was prepared from α-bromo-3,5-dibenzyloxy-acetophenone and 2-(4'-hydroxy-1'naph-thyl)-ethyl-amine.

EXAMPLE 47

Using a procedure analogous to that described in Example 38, 1-(3',5'-dihydroxy-phenyl)-2-[4''-(1''''-naphthyl)-2''-butyl-amino]-ethanol, m.p. 166°–169°C, was prepared from α-bromo-3,5-dibenzyloxy-acetophenone and 4-(1'-naphthyl)-2-butyl-amine.

EXAMPLE 48

Using a procedure analogous to that described in Examples 38, 1-(3',4'-dihydroxy-phenyl)-2-[2''-(4'''-hydroxy-1''''-naphthyl)-ethyl-amino]-ethanol hydrobromide, m.p. 167°–169°C, was prepared from α-bromo-3,4-dibenzyloxy-acetophen-one and 2-(4'-hydroxy-1'-naphthyl)-ethyl-amine,

EXAMPLE 49

Using a procedure analogous to that described in Example 35, 1-(3'-hydroxy-phenyl)-2-[2''-(4'''-methoxy-1''''-naphthyl)-ethyl-amino]-ethanol hydrochloride, m.p. 142°–144°C, was prepared from α-bromo-3-benzyloxy-acetophenone and 2-(4'-methoxy-1'-naphthyl)-ethyl-amine.

EXAMPLE 50

Using a procedure analogous to that described in Examples 35, 1-(4'-hydroxy-phenyl)-2-[2''-(1''''-naphthyl)-ethyl-amino]-ethanol, m.p. 143°–146°C, was prepared from α-bromo-4-benzyloxy-acetophenone and 2-(1'-naphthyl)-ethyl-amine.

EXAMPLE 51

Using a procedure analogous to that described in Example 35, 1-(4'-hydroxy-phenyl)-2-[2''-(4'''-methyl-1''''-naphthyl)-ethyl-amino]-ethanol hydrochloride, m.p. 162°C, was prepared from α-bromo-4-benzyloxy-acetophenone and 2-(4'-methyl-1'-naphthyl)-ethyl-amine.

EXAMPLE 52

Using a procedure analogous to that described in Example 35, 1-(4'-hydroxy-phenyl)-2-[1''-(4'''-methoxy-1''''-naphthyl)-2''-propyl-amino]-ethanol, m.p. 190°–192°C, was prepared from α-bromo-4-benzyloxy-acetophenone and 1-(4'-methoxy-1'-naphthyl)-2-propyl-amine.

EXAMPLE 53

Using a procedure analogous to that described in Example 35, 1-(4'-hydroxy-phenyl)-2-[1''-(4'''-hydroxy-1''''-naphthyl)-2''-propyl-amino]-ethanol hydrochloride, m.p. 199°–202°C, was prepared from α-bromo-4-benzyloxy-acetophenone and 1-(4'-hydroxy-1'-naphthyl)-2-propyl-amine.

EXAMPLE 54

Using a procedure analogous to that described in Example 35, 1-(2'-methyl-4'-hydroxy-phenyl)-2-[2''-methyl-4''-(1'''-naphthyl)-2''-butyl-amino]-ethanol, m.p. 150°C, and its hydrochloride, m.p. 176°–177°C, were prepared from α-bromo-2-methyl-4-benzyloxy-acetophenone and 4-(1'-naphthyl)-2-methyl-2-butyl-amine.

EXAMPLE 55

Using a procedure analogous to that described in Example 35, 1-(4'-hydroxy-phenyl)-2-[2''-methyl-4''-(2'''-methyl-1'''-naphthyl)-2''-butyl-amino]-ethanol, m.p. 188°C, and its hydrochloride, m.p. 168°–170°C, were prepared from α-bromo-4-benzyloxy-acetophenone and 4-(2'-methyl-1'-naphthyl)-2-methyl-2-butyl-amine.

EXAMPLE 56

Using a procedure analogous to that described in Example 38, 1-(2'-methoxy-3',4'-dihydroxy-phenyl)-2-[2''-methyl-4''-(2'''-methyl-1''''-naphthyl)-2''-butyl-amino]-ethanol hydrochloride, m.p. 143°C (decomp.), was prepared from α-bromo-2-methoxy-3,4-dibenzyloxy-acetophenone and 4-(2'-methyl-1'-naphthyl)-2-methyl-2-butyl-amine.

The compounds according to the present invention, that is, those embraced by formula I above and their non-toxic, pharmacologically acceptable acid addition salts, have useful pharmacodynamic properties. More particularly, the compounds of the present invention exhibit very effective and long-lasting peripheral vasodilating, antipruritic, antiallergic, bronchospasmolytic and uterospasmolytic activities in warm-blooded animals, such as guinea pigs and dogs, with distinctly lesser undesirable side effects than known compounds having the same pharmacodynamic properties.

A particularly preferred sub-generic class of compounds are those compounds of the formula I wherein A is di or trimethylene whose carbon atom adjacent to the nitrogen atom has one or two methyl substituents attached thereto; $R_1$ is hydrogen or identical to the $-OR_6$ substituent on the phenyl moiety; $R_2$ is hydrogen; $R_4$ is hydrogen, methyl or methoxy; and $R_5$ is hydrogen, identical to the $-OR_6$ substituent or methanesulfonamido ($CH_3-SO_2-NH-$); and non-toxic, pharmacologically acceptable acid salts thereof.

For pharmaceutical purposes the compounds according to the present invention are administered to warm-blooded animals perorally, parenterally or topically as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories, tinctures, ointments, aerosols and the like.

The single effective dose for oral administration is about 0.033 to 1.34 mgm/kg, preferably 0.083 to 0.34 mgm/kg body weight.

For parenteral administration as bronchospasmolytics, the compounds of the instant invention are applied as solutions comprising a single effective dose of about 0.83 to 0.084 mgm/kg body weight.

For parenteral administration as vasodilators a higher single dosage of about 0.0083 to 0.34 mgm/kg body weight is required.

In the case of aerosols, these are preferably dispensed by means of metering devices which emit about 0.05 to 2 mgm of active ingredient per stroke.

The following examples illustrate a few pharmaceutical compositions comprising a compound of the present invention as an active ingredient and represent the best modes contemplated of putting the invention to practical use. The parts are parts by weight unless otherwise specified.

EXAMPLE 57

Tablets

The tablet composition was compounded from the following ingredients:

| | |
|---|---|
| 1-(4'-Hydroxy-phenyl)-2-[2''-methyl-4''-(1'''-naphthyl)-2''-butyl-amino]-ethanol hydrochloride | 5 parts |
| Stearic acid | 6 " |
| Dextrose | 589 " |
| Total | 600 parts |

Preparation

The ingredients were intimately admixed with each other, and the mixture was compressed into 600 mgm-tablets in a conventional tablet-making machine. Each tablet contained 5 mgm of the active ingredient and, when administered perorally to a warm-blooded animal of about 60 kg body weight in need of such treatment, produced very effective bronchospasmolytic and peripheral vasodilating actions.

Analogous results were obtained with 500 mgm- and 750 mgm-tablets, respectively, manufactured in the same manner from the following ingredients:

| | | |
|---|---|---|
| (a) | 1-(4'-Hydroxy-phenyl)-2-[2''-(1'''-naphthyl)-ethyl-amino]-ethanol hydrochloride | 25 parts |
| | Stearic acid | 6 " |
| | Dextrose | 469 " |
| | Total | 500 parts |
| (b) | 1-(4'-Hydroxy-phenyl)-2-[1''-(4'''-hydroxy-1'''-naphthyl)-2''-propyl-amino]-ethanol hydrochloride | 50 parts |
| | Stearic acid | 8 " |
| | Dextrose | 692 " |
| | Total | 750 parts |

EXAMPLE 58

Ointment

The ointment composition was compounded from the following ingredients:

| | |
|---|---|
| 1-(4'-Hydroxy-phenyl)-2-[2''-(1'''-naphthyl)-ethyl-amino]-ethanol hydrochloride | 0.200 parts |
| Fuming hydrochloric acid | 0.011 " |
| Sodium pyrosulfide | 0.050 " |
| Mixture of equal parts of cetyl alcohol and stearyl alcohol | 18.000 " |
| White vaseline | 5.000 " |
| Synthetic bergamot oil | 0.075 " |
| Distilled water q.s.ad | 100.000 " |

Preparation

The ingredients were compounded in customary fashion into an ointment which contained 0.2% by weight of the active ingredient and, when topically applied to the affected skin area of a warm-blooded animal, produced a very effective antipruritic action.

EXAMPLE 59

Inhalation aerosol

The aerosol spray composition was compounded from the following ingredients:

| | |
|---|---|
| 1-(2'-Methoxy-3',4'-dihydroxy-phenyl)-2-[2''-methyl-4''-(1'''-naphthyl)-2''-butyl-amino]-ethanol hydrochloride | 0.20 to 5.00 parts |
| Soybean lecithin | 0.05 " |
| Propellant gas mixture (Frigen 11, 12 and 114) q.s.ad | 100.00 " |

Preparation

The active ingredient and the lecithin were filled into aerosol containers, and these were then pressurized with the propellant gas mixture in customary fashion; the aerosol containers were equipped with metering valves which dispensed an aerosol spray with from 0.05 to 2 mgm of the active ingredient upon each actuation of the valve. When the aerosol dispensed by one actuation of the metering valve was inhaled by a warm-blooded animal of about 60 kg body weight in need of such treatment, a very effective bronchospasmolytic action was produced.

EXAMPLE 60

Hypodermic solution

The solution was compounded from the following ingredients

| | |
|---|---|
| 1-(2'-Methoxy-3',4'-dihydroxy-phenyl)-2-[2''-methyl-4''-(1'''-naphthyl)-2''-butyl-amino]-ethanol hydrochloride | 0.1 parts |
| Sodium pyrosulfite | 0.1 " |
| Disodium salt of EDTA | 0.5 " |
| Sodium chloride | 8.5 " |
| Double-distilled water q.s.ad | 1000.0 " |

Preparation

The active ingredient and the excipients were dissolved in a sufficient amount of double-distilled water, the solution was diluted with the remaining amount of water and filtered until free from suspended matter, and the filtrate was filled into 1 ml-ampules under aseptic conditions. The filled ampules were then sterilized at 120°C for 20 minutes and sealed. Each ampule contained 0.1 mgm of the active ingredient, and when the contents thereof were administered intravenously to a warm-blooded animal of about 60 kg body weight in need of such treatment, a very effective peripheral vasodilating action was produced.

The same results were obtained with a hypodermic solution compounded in like manner from the following ingredients:

| | | |
|---|---|---|
| 1-(4'-Hydroxy-phenyl)-2-[2''-methyl-4''-(1'''-naphthyl)-2''-butyl-amino]-ethanol hydrochloride | | 20.0 parts |
| Sodium pyrosulfite | | 0.1 " |
| Disodium salt of EDTA | | 2.0 " |
| Double-distilled water | q.s.ad | 1000.0 " |

Analogous results were obtained when any one of the other compounds embraced by formula I or a non-toxic acid addition salt thereof was substituted for the particular active ingredient in Examples 57 through 60. Likewise, the amount of active ingredient in these illustrative examples may be varied to achieve the concentration ranges set forth above, and the amounts and nature of the inert pharmaceutical carrier ingredients may be varied to meet particular requirements.

While the present invention has been illustrated with the aid of certain specific embodiments thereof, it eill be readily apparent to others skilled in the art that the invention is not limited to these particular embodiments, and that various changes and modifications may be made without departing from the spirit of the invention or the scope of the appended claims.

We claim:
1. A racemic mixture of a compound of the formula

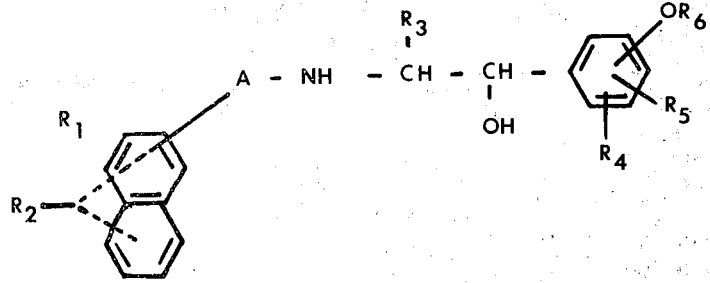

wherein
A is alkylene of 2 to 6 carbon atoms,
$R_1$ is hydrogen, lower alkyl, lower alkoxy or hydroxyl,
$R_2$ is hydrogen, lower alkyl or lower alkoxy,
$R_3$ is hydrogen, methyl or ethyl,
$R_4$ is hydrogen, lower alkyl or lower alkoxy,
$R_5$ is hydrogen or hydroxyl, and
$R_6$ is hydrogen, an optically active antipode component thereof, or a non-toxic, pharmacologically acceptable acid addition salt of said racemic mixture or optically active antipode.

2. A racemic mixture of a compound of the formula

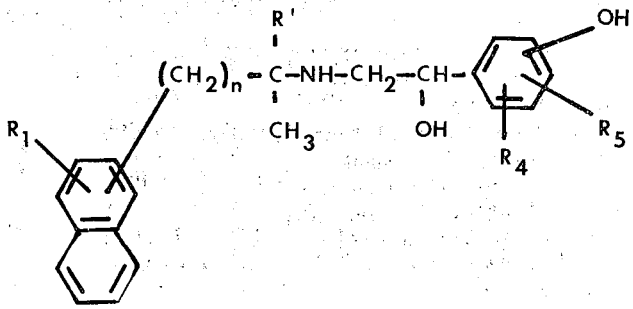

wherein
$R_1$ is hydrogen or hydroxyl,
$R_4$ is hydrogen, methyl or methoxy,
$R_5$ is hydrogen or hydroxyl,
$R'$ is hydrogen or methyl, and
$n$ is 1 or 2,
an optically active antipode component thereof, or a non-toxic, pharmacologically acceptable acid addition salt of said racemic mixture or optically active antipode.

3. A compound according to claim 2, which is 1-(2'-methoxy-3',4'-dihydroxy-phenyl)-2-[2''-methyl-4''-(1'''-naphthyl)-2''-butyl-amino]-ethanol or a non-toxic, pharmacologically acceptable acid addition salt thereof.

4. A compound according to claim 2, which is 1-(3',5'-dihydroxy-phenyl)-2-[2''-(4'''-hydroxy-1'''-naphthyl)-ethyl-amino]-ethanol or a non-toxic, pharmacologically acceptable acid addition salt thereof.

5. A compound according to claim 2, which is 1-(4'-hydroxy-2'-methyl-phenyl)-2-[2'-methyl-4''-(1'''-naphthyl)-2''-butyl-amino]-ethanol or a non-toxic, pharmacologically acceptable acid addition salt thereof.

6. A compound according to claim 2, which is 1-(4'-hydroxy-phenyl)-2-[2''-methyl-4''-(1'''-naphthyl)-2''-butyl-amino]-ethanol or a non-toxic, pharmacologically acceptable acid addition salt thereof.

7. A compound according to claim 2, which is 1-(4'-hydroxy-phenyl)-2-[1''-(4'''-hydroxy-1'''-naphthyl)-2''-propyl-amino]-ethanol or a non-toxic, pharmacologically acceptable acid addition salt thereof.

* * * * *